United States Patent [19]

MacLeod

[11] Patent Number: 5,231,108
[45] Date of Patent: * Jul. 27, 1993

[54] CHEMOPREVENTION OF ELECTROPHILIC DAMAGE BY MERCAPTOPURINE ANALOGS

[75] Inventor: Michael C. MacLeod, Austin, Tex.

[73] Assignee: The Board of Regents, The University of Texas System, Austin, Tex.

[*] Notice: The portion of the term of this patent subsequent to Jun. 9, 2009 has been disclaimed.

[21] Appl. No.: 832,990

[22] Filed: Mar. 4, 1992

Related U.S. Application Data

[60] Division of Ser. No. 583,489, Sep. 17, 1990, Pat. No. 5,120,753, and a continuation-in-part of Ser. No. 262,880, Oct. 26, 1988, abandoned.

[51] Int. Cl.$^5$ .............................................. A61K 31/41
[52] U.S. Cl. ................................................... 514/363
[58] Field of Search ......................................... 514/363

[56] References Cited

U.S. PATENT DOCUMENTS

| | | | |
|---|---|---|---|
| 2,819,198 | 1/1958 | Goohue | 167/42 |
| 4,400,196 | 8/1983 | Albrecht | 71/86 |
| 4,594,096 | 10/1986 | Albrecht | 71/93 |

FOREIGN PATENT DOCUMENTS 0160182  11/1985  European Pat. Off. ............ 514/521

OTHER PUBLICATIONS

CA:104:2187f, Wright et al 1986.

*Primary Examiner*—S. J. Friedman
*Attorney, Agent, or Firm*—Arnold, White & Durkee

[57] ABSTRACT

Analogs of 6-mercaptopurine have been found to enhance the detoxification of various electrophilic toxicants in vivo, while having minimal cytotoxicity themselves. This property allows such compounds to act as scavengers for electrophilic toxicants, thereby preventing the cellular damage caused by such toxic agents.

7 Claims, 2 Drawing Sheets

CHEMOPREVENTION OF ELECTROPHILIC DAMAGE BY MERCAPTOPURINE ANALOGS

The U.S. government may own certain rights in this invention pursuant to NIEHS grant no. ES03602.

This application is a divisional of U.S. Ser. No. 583,489, filed on Sep. 17, 1990, which is now U.S. Pat. No. 5,120,753, and is a continuation-in-part of U.S. Ser. No. 262,880, filed on Oct. 26, 1988 now abandoned.

BACKGROUND OF THE INVENTION

The present invention relates to a method of preventing cellular damage caused by electrophilic toxic, carcinogenic, or mutagenic agents.

It is well known that some chemical compounds are carcinogenic. Further, it is widely accepted that most chemical carcinogens either are strongly electrophilic or are metabolized by cellular enzymes to electrophilic derivatives. These electrophilic "ultimate" carcinogens react with nucleophilic groups in cellular macromolecules, and it is the macromolecular damage which leads to carcinogenesis, mutagenesis and toxicity. Classes of carcinogens which appear to act in this way include aromatic amines, the polycyclic aromatic hydrocarbons, nitrosamines and nitrosamides, and nitrogen mustards. In addition, some therapeutic toxicants, e.g. those used in cancer chemotherapy, may act in this way or may produce undesirable side effects through this mechanism. One strategy for intervention in these processes would be to provide a chemical scavenger of the toxic electrophiles, which would prevent macromolecular damage by prior reaction with the ultimate carcinogen.

This strategy has achieved limited success with two sets of compounds. The first set includes several phenolic plant compounds, exemplified by ellagic acid. These compounds scavenge electrophiles well in vitro, but have limited ability to block polycyclic aromatic hydrocarbon-included carcinogenesis in vivo. This is presumably due to problems with the pharmacokinetics of the compounds. A second set is the dithio-thiones. These were designed to be limited to direct acting, gut carcinogens since the chemopreventive compounds are not taken up by cells. This limits problems due to side effects, but also drastically restricts the range of carcinogens and target tissues to which the strategy is applicable.

In general, the limitations to the success of the nucleophilic scavenging strategy of chemoprevention are: 1) the production of undesirable side effects; 2) inability to achieve therapeutic concentrations intracellularly; and 3) inability to colocalize with the often hydrophobic carcinogens within subcellular compartments.

It is clear that the major xenobiotic metabolizing system of mammalian cells, the cytochrome P450 system, is microsomal in origin. For carcinogens such as the polycyclic aromatic hydrocarbons, which require metabolic activation, this is thought to lead to preferential localization of the metabolites in cellular membranes. Indeed, tests using a highly reactive, ultimate carcinogen derived from benzo(a)pyrene have shown that a pool of membrane-localized electrophile remains active in DNA binding for relatively long periods of time. Similar conclusions have been reached for the same electrophile in two-stage mouse skin carcinogenesis. Therefore, a potential chemopreventive agent should meet four criteria:

1. The agent should facilely detoxify electrophilic carcinogens, either by forming a covalent adduct or by catalysing other detoxification reactions or both;
2. The agent should be a substrate for an endogenous cellular transport system to ensure that it quickly reaches and maintains therapeutic intracellular concentrations;
3. The agent should have enough hydrophobic character to allow it to colocalize with those carcinogens which are hydrophobic; and
4. Toxicity should be minimal.

The compound 6-mercaptopurine (6-MP) has been found to satisfy the first three criteria. In addition, it is able to inhibit several biological activities (DNA damage, mutagenesis) of an ultimate carcinogen in Chinese hamster ovary cells. However, 6-MP is used as a cytotoxic agent in the treatment of childhood leukemia and therefore fails to meet the fourth criterion.

Therefore, a need exists for chemopreventive agents which can satisfy all these criteria.

SUMMARY OF THE INVENTION

A method in accordance with the present invention of detoxifying electrophilic toxicants includes the step of administering to an animal an effective amount of a compound having a low level of cytotoxicity, said compound being a substrate for an endogenous cellular transport system, said compound being selected from the group consisting of compounds having the formula:

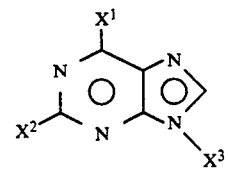

and compounds having the formula:

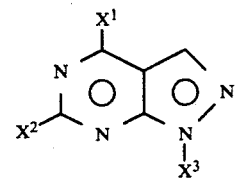

One of $X^1$, $X^2$, and $X^3$ is a thiol having from 0–10 carbons, while another of $X^1$, $X^2$, and $X^3$ is selected from the group consisting of halogens, thiols having from 0–10 carbons, aliphatic and aromatic hydrocarbons having from 1–18 carbons, and $OR^1$, where $R^1$ is selected from the group consisting of hydrogen and aliphatic and aromatic hydrocarbons having from 1–18 carbons. The remaining one of $X^1$, $X^2$, and $X^3$ is selected from the group consisting of H, halogens, thiols having 0–10 carbons, aliphatic and aromatic hydrocarbons having 1–18 carbons, and $OR^2$, where $R^2$ is selected from the group consisting of H and aliphatic and aromatic hydrocarbons having 1–18 carbons.

In this patent, "aliphatic and aromatic hydrocarbons" is used to mean both unsubstituted and substituted hydrocarbons. "Toxicants" is used to mean agents which have toxic, carcinogenic, and/or mutagenic effects. Further, "detoxifying" is used to mean substantially reducing the toxic, carcinogenic, or mutagenic properties of a chemical agent.

In the embodiment of the present invention described above, the thiol groups preferably have from 0-4 carbons, and the aliphatic and aromatic hydrocarbons preferably have from 1-6 carbons.

In another embodiment of the present invention, the method makes use of chemopreventive agents having one of the following two formulas:

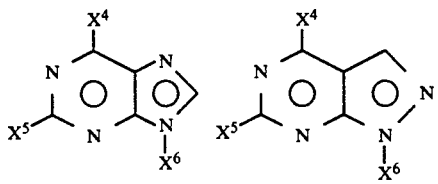

In this embodiment, $X^4$ is a thiol having 0-10 carbons, and $X^5$ and $X^6$ are each independently selected from the group consisting of H, halogens, thiols having 0-10 carbons, aliphatic and aromatic hydrocarbons having 1-18 carbons, and $OR^1$, where $R^1$ is selected from the group consisting of H and aliphatic and aromatic hydrocarbons having 1-18 carbons. Only one of $X^5$ and $X^6$ can be H. $X^4$ is preferably SH, and the thiol groups from which $X^5$ and $X^6$ can be selected preferably have 0-4 carbons, while the aliphatic and aromatic hydrocarbons preferably have 1-6 carbons.

In another embodiment of the present invention, $X^4$ is a thiol having 0-4 carbons, $X^5$ is selected from the group consisting of H, thiols having 0-4 carbons, hydroxyl, and alkyl having 1-6 carbons. $X^6$ is selected from the group consisting of H, SH, and alkyls having 1-6 carbons. Again, only one of $X^5$ and $X^6$ can be H. In a preferred form of this embodiment, $X^4$ is SH, $X^5$ is selected from the group consisting of H, SH, hydroxyl, and methyl, and $X^6$ is selected from the group consisting of H, SH, and methyl.

The present invention provides a method of detoxifying electrophilic toxicants in vivo in animals, such as mammals. Specific examples of animals with respect to which the present invention should be useful include humans, and various avian species. In a particular embodiment of the invention, the method can be used to detoxify in vivo mixtures of toxicants in which polycyclic aromatic hydrocarbons are a major component. The method makes use of chemopreventive agents which contain a thiol group, and therefore can facilely detoxify electrophilic carcinogens, either by forming a covalent adduct, or by catalyzing other detoxification reactions, or both. The agents are substrates for endogenous cellular transport systems, which insures that they will quickly reach and maintain therapeutic intracellular concentrations. Further, the chemopreventive agents have enough hydrophobic character to allow them to co-localize within subcellular compartments with those carcinogens which are hydrophobic. Finally, but quite importantly, the chemopreventive agents used in the method of the present invention are not incorporated into cellular nucleic acids at levels sufficient to produce significant toxicity. Thus, the method claimed in this patent produces minimal undesirable side effects.

Because the chemopreventive agents of the present invention are sufficiently similar to purine, they take advantage of the endogenous purine transporter to rapidly achieve and maintain useful intracellular concentrations of the chemopreventive agents. Since the toxicity of 6-mercaptopurine (6-MP) is known to result from its incorporation into cellular nucelotide pools and nucleic acids, and since the facile reaction of 6-MP with a model electrophile is mediated through the thiol moiety at carbon 6, it is believed that analogs of 6-MP which contain the reactive thiol but are unable to enter nucleotide pools due to their chemical substituents (e.g. at the 9 position) should satisfy all four criteria outlined above. Thus, methods in accordance with the present invention have the potential to prevent the biological damage produced by electrophilic carcinogens and other toxicants.

DETAILED DESCRIPTION OF SPECIFIC EMBODIMENTS

Figure 1:
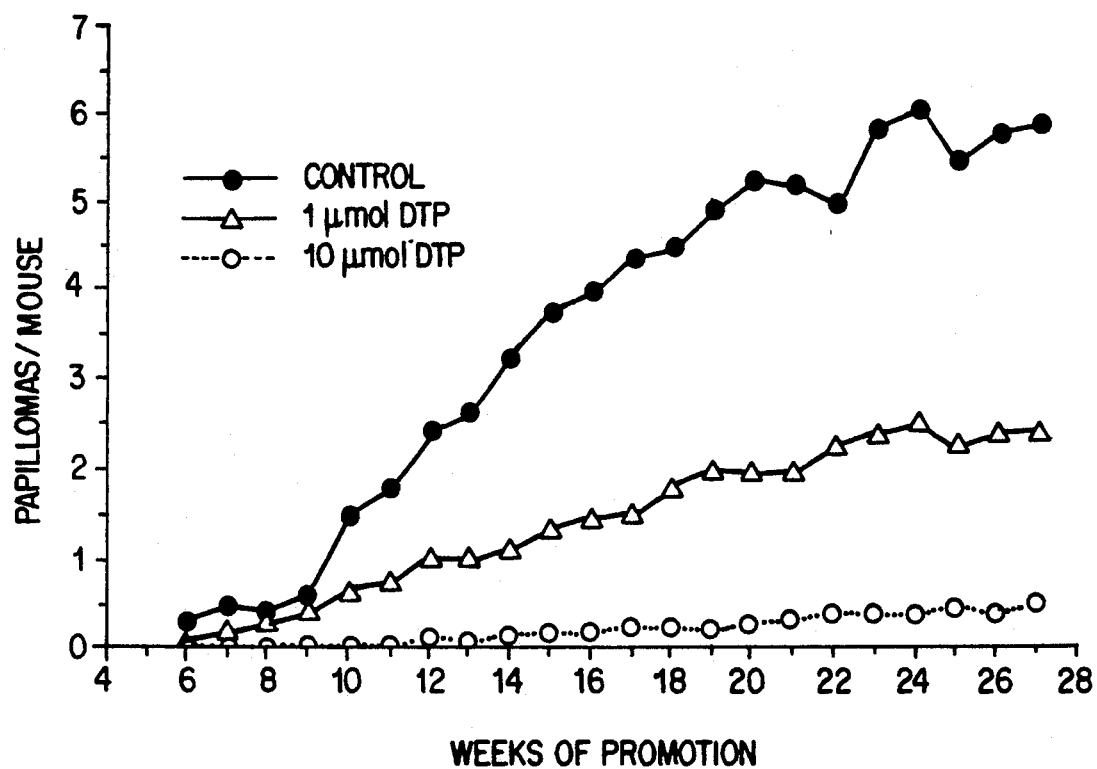
FIG. 1 is a graph showing the effect of dithiopurine on tumorigenesis in mice.

The electrophilic toxicants which the methods of the present invention can detoxify are believed to include those listed below. The list includes 7 classes of compounds, with one or two examples of each, which are known to cause cancer in experimental animals and are thought to be important in human carcinogenesis. Each of the classes of compounds is thought to produce the DNA damage which initiates carcinogenesis by way of one or more electrophilic intermediates. Because of the importance of these electrophilic intermediates, it is believed that nucleophilic scavenging agents in accordance with the present invention will be effective against many or all of these toxicants. The list is meant to be illustrative only, not exhaustive. In addition, it is likely that there exist other electrophilic toxicants not on the list (e.g. other components of tobacco smoke), possibly undescribed, which will also be effectively scavenged by the mercaptopurine analogs.

1. Polynuclear Aromatic Hydrocarbons
Benzo(a)pyrene
3-methylcholanthrene
2. Aromatic Amines
Acetyl aminofluorene
Benzidine
3. Nitro-aromatics
6-nitro benzo(a)pyrene
1,8-dinitropyrene
4. Alkylating Agents
Dimethyl sulfate
Ethylnitrosourea
5. Natural Products
Aflatoxin B1
Safrole
6. Tobacco-specific Carcinogens
4-(methylnitrosamino)-1-(3-pyridyl) -1-butanone (NNK)
7. Chemotherapy Agents
Nitrogen mustards
Cisplatin At least some of the compounds described in this patent are available from Aldrich Chemical Co. (Milwaukee, WI) or Sigma Chemical Co. (St. Louis, MO). Further, compounds in accordance with the present invention can be synthesized by the procedure described in Robins, J. Am. Chem. Soc. 78:784 (1956);

Beaman, J. Am. Chem. Soc. 76:5633 (1954) and Fischer, Ber. 31:431 (1898), all of which are incorporated herein by reference.

For example, as described by Beaman, 2-hydroxy-6-MP can be prepared by adding 15.1 g of xanthine and 81 g of phosphorous pentasulfide to 1350 ml of stirred, dry reagent pyridine. After stirring and refluxing for 3.5 hours, the hot solution was decanted from 0.55 g of solid into 8 l of water plus ice. This formed a solid which remained insoluble on addition of dilute NaOH solution and was discarded. The filtrate from this solid made acid with acetic acid, was boiled down to about 4.5 l and cooled, forming 11.2 g of an orange-brown solid. Trituration with acetone removed much of the dark color. The remaining solid was dissolved in a solution of 7.5 g of NaOH in about 650 ml of water, the solution treated with charcoal and filtered, and the filtrate heated to boiling and made acid with acetic acid. A light yellow solid formed which weighed 8.06 g (50%) based on the weight of xanthine which dissolved.

Likewise, as described by Beaman, 2,6-dithiopurine can be prepared by adding 2-thio-6-hydroxypurine (50 g) and 200 g of phosphorus pentasulfide to 1750 ml of stirred, dry reagent pyridine. The mixture was refluxed for 1.5 hours and the resulting red-black solution allowed to cool about 10 minutes with stirring. It was then poured with stirring into a solution of 663 g of NaOH in 5 l of water plus ice. The two layers which formed were thoroughly shaken in a separatory funnel and separated. The pyridine layer was washed with a cold solution of 70 g of NaOH in 500 ml of water, and this was combined with the main aqueous layer which was then acidified with 1200 ml of glacial acetic acid. The mixture was cooled in ice, and the brown solid which formed was collected and washed with water. After air drying it weighed 44 g (80% crude yield). For purification the crude material was dissolved in a solution of 22 g of NaOH in about 4 l of water and the solution filtered from a little insoluble solid. The filtrate was treated with charcoal, filtered, and the boiling filtrate acidified with acetic acid. The solid which formed on cooling was purified again in the same way to give 30.7 g (56%) of pure light yellow crystalline material.

Other chemopreventive agents of the present invention can be synthesized using generally similar procedures. In general, the synthesis procedures needed would be known to those skilled in the art.

EXAMPLE 1

Chemopreventive agents in accordance with the present invention have been tested for their ability to enhance the detoxification of the model electrophilic carcinogen 7r, 8t-dihydroxy-9t-10t-epoxy-7,8,9,10-tetrahydrobenzo(a)pyrene(BDPE-I). Assays were performed both on an in vitro system and Chinese hamster ovary (CHO) cells.

The assays were performed with seven analogs of 6-MP. These included 6-MP substituted at the 2-position with methyl-, hydroxyl-, and thiosubstituent groups, 9-methyl-6-MP, a thio-substituted imidazole, and 4-mercapto-1H-pyrazolo(3,4-d)pyrimidine (hereafter identified as thiopurinol.) Test chemicals were the highest purity available from either Aldrich (Milwaukee, WI) or Sigma (St. Louis, MO), and were used without further purification. Unlabeled BPDE-I and [3H]-BPDE-I were obtained from the NCI's Chemical Carcinogen Standard Repository. Tock solutions (32–500 $\mu$M) were prepared in absolute ethanol and stored at $-20°$ C. Concentrations and reactivity were verified by absorbance and fluorescence spectrophotometry. Concentrated stock solutions of the thiol compounds to be tested were prepared in 0.1 N NaOH.

To directly measure the ability to enhance the detoxification of BPDE-I, aqueous reaction mixtures containing 5 $\mu$M BPDE-I and 15–60 $\mu$M test compound in a supporting solvent containing 50 mM Tris pH 7.5 were monitored spectrophotometrically at 352 nm. Formation of adducts between the carcinogen and the thiol results in an increase in absorbance at 352 nm. This reaction is pseudo-first order, and the observed rate constant at any concentration of thiol can be obtained by curve-fitting. The observed rate constant increases linearly with concentration of thiol at low concentrations, and the slope of this line, $k$cat, is a measure of the test compound's ability to detoxify the BPDE-I. These results are given in table 1 below. By this assay, 9-methyl-6-MP is similar to 6-MP in catalysis of detoxification, and 2-methyl-6-MP and thiopurinol have significant activity.

A more relevant test depends on the ability of BPDE-I to bind covalently to DNA in vitro. Addition of increasing amounts of thiol test compounds to reaction mixtures containing constant amount of [3H]-BPDE-I (1.6 $\mu$M) and purified DNA (45 $\mu$g/mL) inhibits the covalent binding of BPDE-I to the DNA. When this inhibition is expressed as a reciprocal (adduct level in the absence of test compound/adduct level in the presence of test compound) a linear relation is obtained, in which the slipe of the line is a measure of the ability of the compound to compete with DNA for binding of the electrophilic carcinogen. In Table 1, this measure ($k$cat/$k$DNA) has been tabulated for each of the 6 compounds tested. It can be seen that 3 compounds (9-methyl-6-MP, 2,6-dithiopurine and thiopurinol) have activities comparable to or higher than 6-MP, while 2-OH-6-MP and 2-methyl-6-MP also have significant activity.

Direct tests of the ability of the compounds to block the deleterious effects of the carcinogen in intact, mammalian cells were carried out. Cultures of AT3-2 cells, a subline of CHO cells, were maintained, treated with 1.0 $\mu$M BPDE-I for 60 minutes, and analyzed for covalent binding to DNA as previously described by MacLeod et al (1987) Chem.-Biol. Interact. 63:279–289, which is incorporated herein by reference.

BPDE-I binds covalently to cellular DNA when added to the culture medium of CHO cells. The inhibition of this binding by the addition of thiopurines at a final concentration of either 12 $\mu$M or 120 $\mu$M was tested, and the results are shown in table 1 below. Four of the compounds tested (9-methyl-6-MP, 2,6-dithiopurine, thiopurinol, and 2-methyl-6-MP) exhibited activity comparable to or higher than 6-MP in the CHO cell assay. The remaining compounds showed lower but still significant activity. Other thiol-containing compounds with structures unrelated to 6-MP, specifically 2-mercaptoethanol and mercaptoethanesulfonic acid, were ineffective in this assay.

TABLE 1

| Compound | $k$cat ($\times 10^4$; $M^{-1}sec^{-1}$) | Inhibition of DNA binding ($k$cat/$k$DNA) | Inhibition of Cellular DNA binding at: | |
|---|---|---|---|---|
| | | | 12 $\mu$M | 120 $\mu$M |
| 9-methyl-6-MP | 1.83 | 2.82 | 67.6% | 95.3% |
| 2,6-dithio-purine | n.d.** | 0.773 | 61.6 | 94.7 |
| thiopurinol | 0.64 | 1.096 | 43.4 | 89.6 |
| 6-MP | 1.78 | 0.891 | n.d. | 81.7 |

TABLE 1-continued

| Compound | $k_{cat}$ (× 10⁴; M⁻¹sec⁻¹) | Inhibition of DNA binding ($k_{cat}/k_{DNA}$) | Inhibition of Cellular DNA binding at: | |
|---|---|---|---|---|
| | | | 12 μM | 120 μM |
| 2-methyl-6-MP | 0.82 | 0.595 | 36.1 | 79.1 |
| 2-OH-6-MP | 0.31 | 0.427 | 27.6 | 76.7 |
| 2-Cl-6-MP | n.d. | 0.145 | 15.0 | 56.4 |
| MNTI* | n.d. | 0.166 | 4.7 | 31.8 |

*MNTI is 1-methyl-4-nitro-5-thio-imidazole.
**Not determined.

These tests showed that chemopreventive agents of the present invention will enhance the detoxification of BPDE-I and facilely form a chemical adduct with it. Such agents were further found to inhibit the binding of BPDE-I to DNA in Chinese hamster ovary cells (CHO cells) exposed to both compounds. This effect is the basis for the postulated activity in the chemoprevention of carcinogenesis. Inhibition of BPDE-I binding to DNA in CHO cells occurs at concentrations of chemopreventive agent which also inhibit the induction of mutations at the adenosine phosphoribosyl transferase locus in the same cells.

The parent compound, 6-MP, has demonstrated facile reaction with BPDE-I over a wide pH range (6–10) and a wide temperature range (15°–50° C.).

EXAMPLE 2

The effect of the present invention on tumorigenesis was tested as follows. Each experimental group contained 30 female SENCAR mice. A solvent (0.2 mL) consisting of 75% tetrahydrofuran:24.9% dimethylsulfoxide:0.1% triethylamine was applied topically to the shaken backs of the mice containing either no test compound (control) or 1.0 or 10.0 μmol of either 2,6-dithiopurine or thiopurinol. Fifteen minutes later, an initiating dose of BPDE-I (200 nmol in 0.2 mL tetrahydrofuran) was applied to the same area. After 2 weeks, twice weekly application of the tumor promoter TPA was begun and carried out for 23 weeks. The appearance of skin tumors (papillomas) on the backs of the treated mice was recorded weekly for the duration of the experiment. In these experiments, the incidence of skin tumors is very low in mice which do not receive the initiating BPDE treatment.

Figure 2:
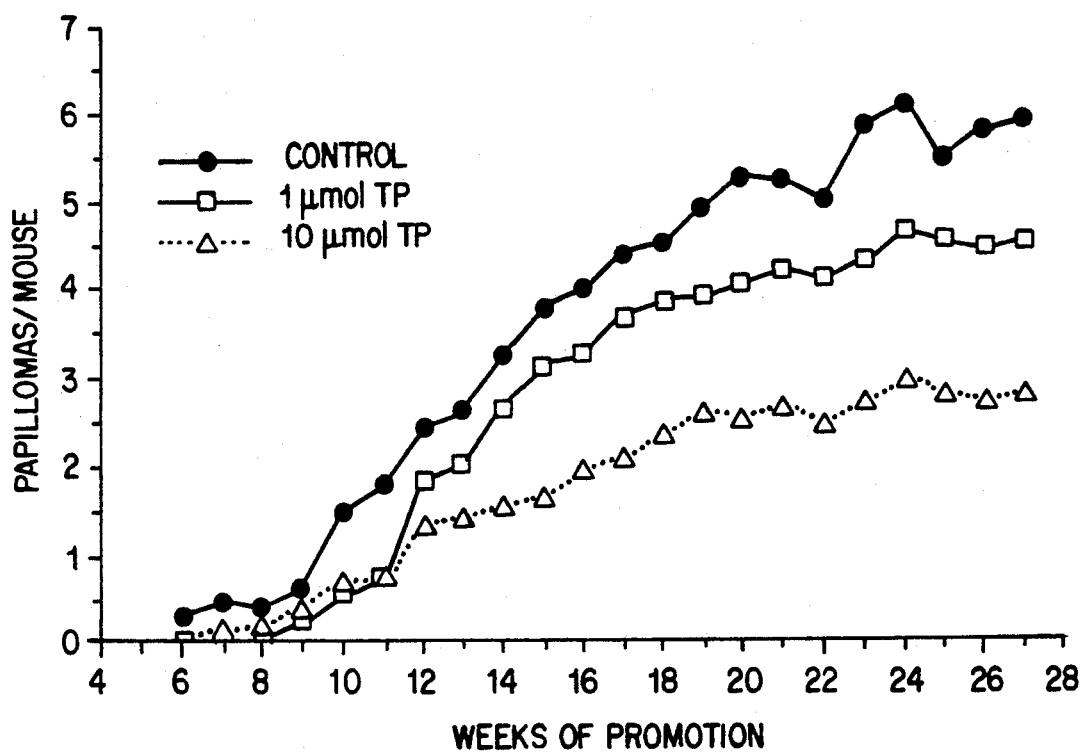
FIG. 2 is a graph showing the effect of thiopurinol on tumorigenesis in mice.

In the control animals receiving solvent only, followed by the initiating carcinogen, skin tumors began to appear after 6–8 weeks of promotion; the average number of tumors/mouse increased in a linear fashion throughout the first 20 weeks of promotion, and then began to level out at between 5 and 6 tumors per animal. This is the behavior expected from previous studies with this tumor model. In the animals treated with 2,6-dithiopurine (DTP), there was a clear, dose-dependent decrease in the tumor incidence. At the higher dose, there was about a 90% decrease in tumor incidence. Even at a 10-fold lower dose there was greater than 50% inhibition of tumorigenesis. (See FIG. 1.) Thiopurinol also caused a dose-dependent inhibition of tumor formation; at week 28 the low dose TP group had 24% fewer tumors than the control group and the high dose TP had 58% fewer tumors. (See FIG. 2.) Thus both compounds were capable of significant inhibition of tumor formation.

Chemopreventive agents in accordance with the present invention can suitably be formulated as a composition including an effective amount of one or more of the active agents, and a pharmaceutically acceptable excipient, diluent, or carrier. Compositions in accordance with the present invention will contain between about 0.001% and about 99% by weight active agents, preferably between about 0.001% and about 10%.

Methods in accordance with the present invention comprise administering to an animal an effective amount of the compounds or composition described above. The administering step is preferably by oral dosage, but can also suitably be parenteral and by intraveneous, intraarterial, intramuscular, intralymphatic, intraperitoneal, subcutaneous, intrapleural, or intrathecal injection, or by topical application. Suitable dosages are believed to be in the range of 0.01–100 mg/kg body weight, preferably between 0.1–50 mg/kg.

A nontoxic 6-MP analog could be used as a chronic treatment (e.g. as a dietary supplement) to prevent the initiation of a carcinogenesis by electrophilic carcinogens. This could be in the population as a whole, or in selected high risk populations (e.g. roofers, coke oven workers, cancer patients exposed to electrophiles during chemotherapeutic treatments, or persons with genetically determined high cancer risks). An additional possible commercial use would be as an adjunct, protective therapy in cases where the therapeutic value of another drug is limited by side effects due to metabolism of that drug to an electrophilic form. Thus, in some cases the 6-MP analog might block the side effects without blocking the therapeutic effect.

The description and examples given in this patent are intended to illustrate the present invention. They are not intended to be an exhaustive list of all possible specific embodiments of the present invention. Those skilled in the art will recognize that modifications could be made to the specific embodiments listed here which would still be within the scope of the present invention.

I claim:

1. A method of detoxifying electrophilic toxicants, comprising administering to an animal an effective amount of a compound having a low level of cytotoxicity, said compound being a substrate for an endogenous cellular transport system, said compound having the formula

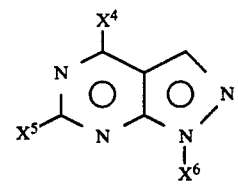

where $X^4$ is a thiol having 0–10 carbons; $X^5$ and $X^6$ are independently selected from the group consisting of H, halogens, thiols having 0–10 carbons, aliphatic and aromatic hydrocarbons having 1–18 carbons, and $OR^1$, where $R^1$ is selected from the group consisting of H and aliphatic and aromatic hydrocarbons having 1–18 carbons; with the limitation that only one of $X^5$ and $X^6$ can be H.

2. The method of claim 1, where $X^4$ is SH.

3. The method of claim 1, where $X^5$ and $X^6$ are independently selected from the group consisting of H, halogens, thiols having 0–4 carbons, aliphatic and aromatic hydrocarbons having 1–6 carbons, and $OR^1$ where $R^1$ is selected from the group consisting of H and aliphatic and aromatic hydrocarbons having 1–6 carbons; with the limitation that only one of $X^5$ and $X^6$ can be H.

4. The method of claim 1, where $X^4$ is SH, and where $X^5$ and $X^6$ are independently selected from the group consisting of H, halogens, thiols having 0-4 carbons, aliphatic and aromatic hydrocarbons having 1-6 carbons, and $OR^1$ is selected from the group consisting of H and aliphatic and aromatic hydrocarbons having 1-6 carbons; with the limitation that only one of $X^5$ and $X^6$ can be H.

5. A method of detoxifying electrophilic toxicants, comprising administering to an animal an effective amount of a compound having a low level of cytotoxicity, said compound being a substrate for an endogenous cellular transport system, said compound having the formula

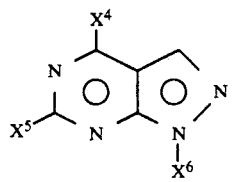

where $X^4$ is a thiol having 0-4 carbons; $X^5$ is selected from the group consisting of H, thiols having 0-4 carbons, hydroxy, and alkyls having 1-6 carbons; and $X^6$ is selected from the group consisting of H and alkyls having 1-6 carbons; with the limitation that only one of $X^5$ and $X^6$ can be H.

6. The method of claim 5, where $X^4$ is SH, $X^5$ is selected from the group consisting of H, SH, hydroxyl, and methyl; and $X^6$ is selected from the group consisting of H, SH, and methyl; with the limitation that only one of $X^5$ and $X^6$ can be H.

7. A method of detoxifying mixtures of toxicants in which polycyclic aromatic hydrocarbons are a major component in vivo in a mammal, comprising administering to an animal an effective amount of a compound having a low level of cytotoxicity, said compound being a substrate for an endogenous cellular transport system, said compound having the formula

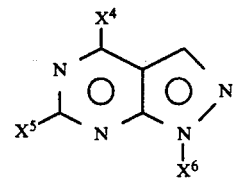

where $X^4$ is a thiol having 0-10 carbons; and $X^5$ and $X^6$ are independently selected from the group consisting of H, halogens, thiols having 0-10 carbons, aliphatic and aromatic hydrocarbons having 1-18 carbons, or $OR^1$, where $R^1$ is selected from the group consisting of H and aliphatic and aromatic hydrocarbons having 1-18 carbons; with the limitation that only one of $X^5$ and $X^6$ can be H.

* * * * *

UNITED STATES PATENT AND TRADEMARK OFFICE
CERTIFICATE OF CORRECTION

PATENT NO. : 5,231,108

DATED : July 27, 1993

INVENTOR(S) : MacLeod

It is certified that error appears in the above-indentified patent and that said Letters Patent is hereby corrected as shown below:

At column 5, line 67, "Tock" should be --Stock--.

At column 6, line 31, "slipe" should be --slope--.

At column 7, line 34, "shaken" should be --shaven--.

Signed and Sealed this

Twenty-ninth Day of March, 1994

Attest:

BRUCE LEHMAN

Attesting Officer

Commissioner of Patents and Trademarks